(12) United States Patent
White

(10) Patent No.: US 8,778,276 B2
(45) Date of Patent: Jul. 15, 2014

(54) DETECTION DEVICE

(75) Inventor: Peter John White, Salisbury (GB)

(73) Assignee: The Secretary of State for Defence (GB)

( * ) Notice: Subject to any disclaimer, the term of this patent is extended or adjusted under 35 U.S.C. 154(b) by 387 days.

(21) Appl. No.: 12/999,064

(22) PCT Filed: Jun. 18, 2009

(86) PCT No.: PCT/GB2009/001522
§ 371 (c)(1),
(2), (4) Date: Jan. 25, 2011

(87) PCT Pub. No.: WO2009/153559
PCT Pub. Date: Dec. 23, 2009

(65) Prior Publication Data
US 2011/0143450 A1    Jun. 16, 2011

(30) Foreign Application Priority Data

Jun. 18, 2008 (GB) .................................. 0811132.0

(51) Int. Cl.
*G01N 21/77* (2006.01)
*G01N 1/20* (2006.01)
*C12M 1/34* (2006.01)

(52) U.S. Cl.
CPC ........ *G01N 21/77* (2013.01); *G01N 2001/2057* (2013.01); *G01N 1/2042* (2013.01); *C12M 1/34* (2013.01)
USPC ............................ 422/420; 422/921; 436/169

(58) Field of Classification Search
CPC .......... G01N 21/77; G01N 2001/2057; G01N 1/2042; C12M 1/34

USPC .................................................. 422/420, 921
See application file for complete search history.

(56) References Cited

U.S. PATENT DOCUMENTS

| 6,258,531 | B1 | 7/2001 | Bienhaus et al. |
| 2005/0136553 | A1 | 6/2005 | Kaylor et al. |
| 2006/0292036 | A1 | 12/2006 | Gould et al. |
| 2007/0110623 | A1 | 5/2007 | Liu |
| 2008/0166820 | A1 | 7/2008 | Gould et al. |

FOREIGN PATENT DOCUMENTS

| EP | 0734749 | 10/1996 |
| GB | 2276002 | 9/1994 |
| GB | 2322192 | 8/1998 |
| GB | 2342443 | 4/2000 |
| GB | 2342993 | 4/2000 |
| GB | 2345133 | 6/2000 |
| GB | 2347500 | 9/2000 |
| GB | 2431240 | 4/2007 |
| GB | 2435832 | 9/2007 |

(Continued)

OTHER PUBLICATIONS

Examination Report dated Oct. 5, 2009 in related Application No. GB0910532.1.
Response to Examination Report dated Jun. 14, 2010 in related Application No. GB0910532.1.

(Continued)

*Primary Examiner* — Robert Xu
(74) *Attorney, Agent, or Firm* — Dean W. Russell; Kristin M. Crall; Kilpatrick Townsend & Stockton LLP

(57) ABSTRACT

The present invention provides devices, in particular lateral flow devices, for detecting a target analyte on a surface, in which the elements of collection and detection are integrated. The present invention also provides methods of use thereof.

9 Claims, 5 Drawing Sheets

(56) References Cited

FOREIGN PATENT DOCUMENTS

Figure 1:
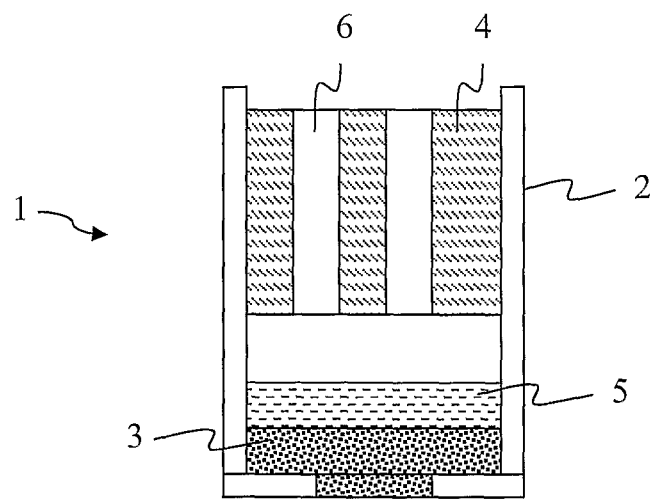

| | | |
|---|---|---|
| GB | 2460956 B | 12/2009 |
| WO | WO-99508761 | 3/1995 |
| WO | WO-0000288 | 1/2000 |
| WO | WO-0057179 | 9/2000 |
| WO | WO-2009036168 | 3/2009 |

OTHER PUBLICATIONS

Examination Report dated Jul. 28, 2010 in related Application No. GB0910532.1.

Response to Examination Report dated Sep. 7, 2010 in related Application No. GB0910532.1.

Certificate of Grant dated Nov. 17, 2010 in related Application No. GB0910532.1.

DETECTION DEVICE

CROSS REFERENCE TO RELATED APPLICATIONS

This application is the U.S. national phase of International Application No. PCT/GB2009/001522 filed on Jun. 18, 2009 and published in English on Dec. 23, 2009 as International Publication No. WO 2009/153559 A1, which application claims priority to Great Britain Patent Application No. 0811132.0 filed on Jun. 18, 2008, the contents of both of which are incorporated herein by reference.

The present invention is concerned with devices for detecting a target analyte on a surface, in particular lateral flow devices, and methods of use thereof.

Lateral flow devices used for detection of a target analyte on a surface commonly comprise four individual elements or components: a vessel containing a liquid, a pipette, a swab and a lateral flow test strip. The liquid is often a low ionic strength buffer such as 10 mM HEPES pH 7.5 or phosphate buffered saline (PBS).

Lateral flow test strips have been a popular platform for rapid diagnostic tests since their introduction in the late 1980s, and may be applied to the specific detection of many analytes, especially antigens or antibodies. A lateral flow test strip comprises a recognition element specific to an analyte of interest. The recognition element is often an antibody. Detection of the specific analyte, via binding to the recognition element, is usually through production of a visual indicator, such as a coloured line on the test strip. Some lateral flow devices allow for the simultaneous analysis of multiple analytes. Lateral flow test strips are chromatographic based in that liquid contacting the test strip flows along the strip through capillary action to contact the immobilised recognition element. The test strip may comprise paper-based products, glass fibres, nitrocellulose or polypropylene. Test strips are also known as immuno-chromatographic test strips.

Lateral flow test strips are simple to use, relatively inexpensive to manufacture, generally have long term stability over a wide range of conditions, produce a result in a relatively short time and are disposable. These features make test strips ideal for applications such as home testing, rapid point of care testing, and testing for various environmental and agricultural analytes. In addition, they provide reliable tests that might not otherwise be available to developing countries. Lateral flow test strips have been used for analysis of a multitude of environmental samples, such as in analysis of water pollution and plant diseases. The lateral flow format is ideal for analysis in harsh environments.

Detection of a target analyte on a surface typically requires the steps of immersing a swab in a suitable buffer solution, swabbing a surface, re-immersing the swab in a buffer solution, and applying an aliquot of the buffer solution to a lateral flow test strip. The sample proceeds along the test strip through capillary action whereupon it contacts the recognition element, with detection of the target analyte usually through production of a visual indicator, such as production of a colour. However, the requirement to use four separate elements in a multi-step procedure can introduce error into an analysis, especially through cross-contamination. There is therefore a requirement for reducing the number of elements, and also the number of steps required in detection of a surface bound target analyte. A single element based test, in which collection, purification and detection are integrated, could significantly reduce the possibility of cross-contamination, false positives and false negatives, and increase user confidence.

Environmental monitoring, especially detection of surface contaminants, presents significant technological challenges. In particular, devices and assays for monitoring should be user friendly and reliable: the risk of user error should be minimised. In particular, lateral flow devices which comprise multiple elements (vessel containing buffer, a pipette, a swab and at least one lateral flow test strip), and require several manipulation steps are by nature prone to user error. These devices are also often difficult to use whilst wearing protective clothing. An integrated collection and detection device however could overcome these limitations.

The present invention thus generally aims to provide a device for detecting a target analyte on a surface, in which the elements of collection and detection are integrated, thus reducing the number of steps required for analysis, and in particular removing the requirement for a discrete collection step.

Accordingly, in a first aspect, the present invention provides a device for detecting a target analyte on a surface comprising a female member having a first region and a second region, a corresponding male member engaged within the first region of the female member which is capable of movement within the female member in response to an applied force, said male member comprising or capable of supporting detection means to the target analyte, and an absorbent material supported within the second region of the female member which is at least partially externally available, whereby in use a fluid absorbed to the absorbent material may be communicated to the detection means.

A female member defines a cavity. The female member of the present invention has a cavity divided into two regions, a first region and a second region, wherein the two regions are suitably adjacent each other along the axis of the cavity. The first region is situated at the opening or entrance end to the female member and provides for engagement of the male member with the female member. The second region is therefore situated at the opposite end, i.e. base, of the female member. The female member is preferably cylindrical, wherein the first region and second region are adjacent each other along the cylindrical axis of the female member.

Communication of the fluid absorbed to the absorbent material may be provided by having the detection means in contact or communication with the absorbent material, however preferably the detection means is discrete from the absorbent material and communication is enabled or facilitated through movement of the male member within the female member.

The device may be provided without the detection means to the target analyte in situ, thus with the device only comprising means capable of supporting the detection means. The detection means could then be inserted into the device before an analysis is undertaken. This would allow for the device to be reusable.

As used herein, detection means denotes any means capable of providing a measurable response to the target analyte upon contact with a fluid containing the target analyte, preferably through use of a recognition element specific to the target analyte. The measurable response is preferably a visual indicator, such as production of a colour via a chemical reaction. The detection means are preferably chromatographic based to facilitate flow of the fluid comprising the target analyte, and in a most preferred embodiment is a lateral flow test strip. The detection means may be capable of detecting multiple target analytes, and may for example comprise multiple lateral flow test strips.

As used herein, communicate denotes either the direct contact of a first entity to a second entity, such as direct contact of the detection means to the absorbent material, or the indirect contact of a first entity to a second entity, through for example an intervening third entity, such as a filtration material, wherein the first entity and second entity are each in direct contact with the third entity.

As used herein, discrete denotes that a first entity and a second entity are not in communication or contact with each other.

The device is chiefly directed to detecting a target analyte on a surface, wherein the absorbent material having a fluid absorbed to the absorbent material may be contacted to the surface. Both absorption of a fluid to the absorbent material, and contact of the absorbent material to the surface are provided by the absorbent material being at least partially externally available. The device could also be used for detecting target analyte in a liquid, such as a bodily fluid or contaminated waste water, wherein contact with the liquid is provided by the absorbent material being at least partially externally available.

The absorbent material supported within the second region of the female member is at least partially externally available preferably through providing an orifice or opening in the female member, generally in the base of the female member. The absorbent material may be capable of rotation within the second region of the female member such that on contact with a surface a more even collection of sample is provided. The absorbent material may for example have a spherical shape. A spherically shaped absorbent material also provides for better contact with uneven surfaces. In use, the absorbent material of the device may be contacted with a fluid, such that the fluid is absorbed to the absorbent material, through the absorbent material being at least partially externally available. The absorbent material may then be placed and/or moved on a surface to collect or absorb surface bound analytes. The fluid may be a buffer solution.

The male member is capable of movement within the female member in response to an applied force. In a preferred embodiment the male member is slidable within the female member. In use, this movement facilitates communication of a fluid absorbed to the absorbent material to the detection means. The movement may for example enable the detection means to move from a position where it is discrete from the absorbent material to a position where it communicates with the absorbent material. Alternatively, the male member may be capable of applying pressure to the adsorbent material such that fluid is released from the adsorbent material and retained in the device. The detection means may then be communicated with the released fluid. The male member may be substantially hollow such that the detection means is supported within the male member. The male member may be capable of independent movement, such as sliding, within the hollow of the male member.

The detection means may be supported by the male member such that the detection means is capable of movement independent of the male member, i.e. applying a force to the male member will provide movement of the male member and the detection means, however applying a force to the detection means will provide movement of the detection means only, and not movement of the male member. The male member is preferably capable of applying pressure to the absorbent material such that the majority (i.e. more than 50%) of any absorbed fluid may be released or squeezed from the absorbent material but remain in the device. This may be enabled by the male member having an orifice or opening, or indeed multiple orifices or openings, situated in a surface of the male member that is capable of communicating with the absorbent material which is greater in surface area than that of the orifice or opening in the female member of the device. On applying pressure to the absorbed material any absorbed fluid therein will be squeezed from the absorbent material and exit through the route of least resistance, i.e. through the orifice or opening of largest surface area. The orifice in the male member is preferably at least twice the surface area of the orifice in the female member. Alternatively, the device may further comprise a removable cap or lid over the orifice or opening in the female member. The cap may thus be removed to enable the absorbent material to be contacted with a surface, and be reattached prior to applying pressure with the male member, thereby ensuring retention of fluid in the device. The cap will in general provide a liquid tight seal.

One method of use of the first aspect comprises collecting or absorbing surface bound analytes to the absorbent material and then contacting or communicating the detection means with either the absorbent material containing the absorbed fluid, or with fluid released from the absorbent material. Preferably absorbed fluid is squeezed from the absorbent material by applying pressure with the male member such that the majority of the released fluid remains in the device. The detection means is then contacted or communicated with the released fluid either automatically, or through movement of the detection means to contact the fluid.

In a second aspect, the present invention provides a device for detecting a target analyte on a surface comprising a vessel defining a cavity having a first region and a second region, wherein the first region comprises or is capable of supporting detection means to the target analyte and an adsorbent material is supported within the second region such that it is at least externally available and the vessel comprises suction means or is adapted such that suction means may be connected to the device, whereby in use a fluid absorbed to the absorbent material may be communicated to the detection means through the use of suction.

The device may for example be adapted for use with a 'pipette boy', a well known laboratory instrument that enables the sucking of liquid via a small pump present in the hand set, wherein the first region of the vessel is adapted to accommodate the teat of the 'pipette boy' such that a seal is made between the teat and the vessel. The device may comprise multiple seals to enable efficient use of any suction applied.

One method of use of the second aspect comprises collecting or absorbing surface bound analytes to the absorbent material and then applying suction to the device such that the absorbed fluid, containing the surface bound analytes, is communicated with the detection means. Features of the second aspect should be arranged to enable efficient suction to be applied to the device.

Both the first and second aspects of the present invention integrate the elements of collection and detection in devices for detecting surface bound target analytes. The devices enable the number of steps required for analysis to be reduced over that of devices in the art, and in particular remove the requirement for a discrete collection step. The devices provide for better handling, better containment, reduced probability of cross contamination, less chance of error, and increased confidence. The devices are potentially forensically contained, reducing or even eradicating the potential of cross-contamination.

The devices are particularly useful for detecting a target biological material or contaminant on a surface. The target biological material may be bacteria, including spores, fungi, viruses, plant cells, insect cells, mammalian cells and cellular constituents such as proteins, lipids, carbohydrates and polynucleotides. The contaminant may alternatively be a chemical material such as a pesticide, explosive or drug. For example, the device may facilitate a spot test for a drug, or antibody based detection of an explosive as known in the art.

The devices require minimal manipulation and can be more easily used by personnel wearing protective clothing than current devices. Such a device would also require minimal training and would be simpler to use than current devices in potentially contaminated environments. Ease of use would also increase user confidence in the test result and reduce operator stress in situations where contamination is suspected. The device could be a single integrated disposable.

The detection means may be removed from the device to enable interrogation of the measurable response or visual indicator. In a preferred embodiment however the device is transparent (i.e. are manufactured from a transparent material) or comprises a window to enable visual inspection of any visual indication of a positive and/or negative result produced by the detection means. The window may further comprise a magnification property to aid visual inspection of any visual indicator.

The devices of the first and second aspects may further comprise a filter material or filter layer situated between the absorbent material and the detection means. The filter material may contact either the absorbent material or the detection means, however the filter material or filter layer is preferably in contact with the absorbent material, and preferably discrete from the detection means and, where applicable, discrete from the male member. The filter material or filter layer may prevent particulate impurities, such as dust, from contacting the detection means, and may especially prevent impurities which may interfere with the test or the function of a recognition element on a lateral flow test strip. The filter layer may for example be a nylon membrane. In one embodiment of the first aspect, the detection means may be capable of communicating with the absorbent material through the filter material, or alternatively the male member may be capable of applying pressure to the absorbent material through applying pressure to the filter material.

The devices may comprise means for storing a fluid discrete from the absorbent material but arranged such that the fluid is capable of being contacted with, and absorbed to, the absorbent material prior to use of the device in detecting a surface bound target analyte. For example, the fluid may be stored in a removable cap or lid over the orifice or opening in the female member. In a preferred embodiment however a fluid is absorbed to the absorbent material, i.e. the absorbent material is pre-wetted. The fluid is preferably a buffer solution, such as for providing conditions suitable for binding of the target analyte to a recognition element on a lateral flow test strip. The buffer solution may be a HEPES buffer containing a detergent. A pre-wetted absorbent material removes any requirement for contacting the device with a discrete fluid or buffer solution before analysis, and thus further reduces the likelihood of cross-contamination and false positive or negative results. It also reduces the possibility of user error. In this embodiment of the device the detection means must be discrete from the absorbent material. The absorbent material may be a sponge-like material.

A device comprising a pre-wetted absorbent material may further comprise means for preventing loss or evaporation of fluid from the absorbent material, especially during storage of the device. Such means may comprise use of one or more airtight foil seals. The foil seals may be removed prior to use of the device, or alternatively may be cut or punctured prior to use.

In a third aspect, the present invention provides a method for detecting a target analyte on a surface comprising the steps of providing a device of the first or second aspect having a fluid absorbed to the absorbent material, contacting the absorbent material of the device with the surface, communicating the fluid to the detection means, and detecting the target analyte through a measurable response provided by the detection means.

The absorbent material is preferably prewetted with the fluid. However, if the absorbent material is not prewetted then the fluid should be absorbed to the absorbent material of the device prior to contacting the absorbent material with the surface.

Communicating the fluid to the detection means may be achieved in the device of the first aspect by applying a force to the male member and/or the detection means such that the detection means communicates with the absorbent material, and thereby the absorbed fluid, or alternatively by applying a force to the male member such that the male member communicates and applies pressure to the absorbent material to release the absorbed fluid into the device. The detection means may thereby be communicated with the released fluid either automatically or by movement of the detection means. Communicating the fluid to the detection means may be achieved in the device of the second aspect by applying suction.

The devices of the present application enable integrated collection, sample processing and detection. Collection is through an absorbent material such as natural or synthetic sponge, which is preferably pre-soaked with a fluid. Suction or compression can be used to facilitate communication of the fluid, potentially containing the target analyte, to the detection means. A filter enables sample processing and in particular removal of impurities, such as particulate material, before communication of the fluid with the detection means. Additional functionality can also be incorporated into the filter, or through additional functional membranes, to separate, remove or select analytes/impurities based on charge, hydrophobicity, size or other biophysical properties.

Figure 2A:
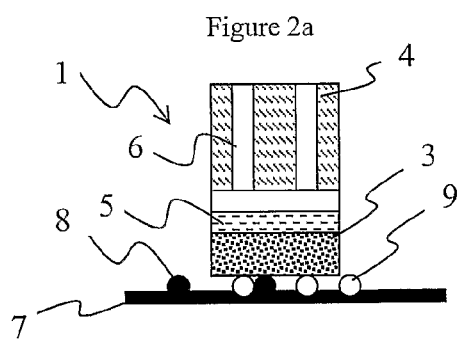
Figure 2B:
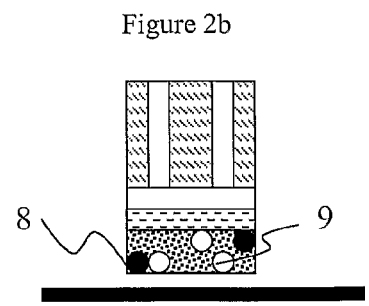
Figure 2C:
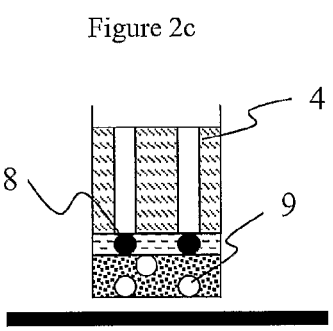
Figure 2D:
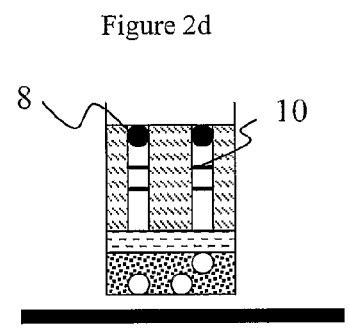
Figure 3:
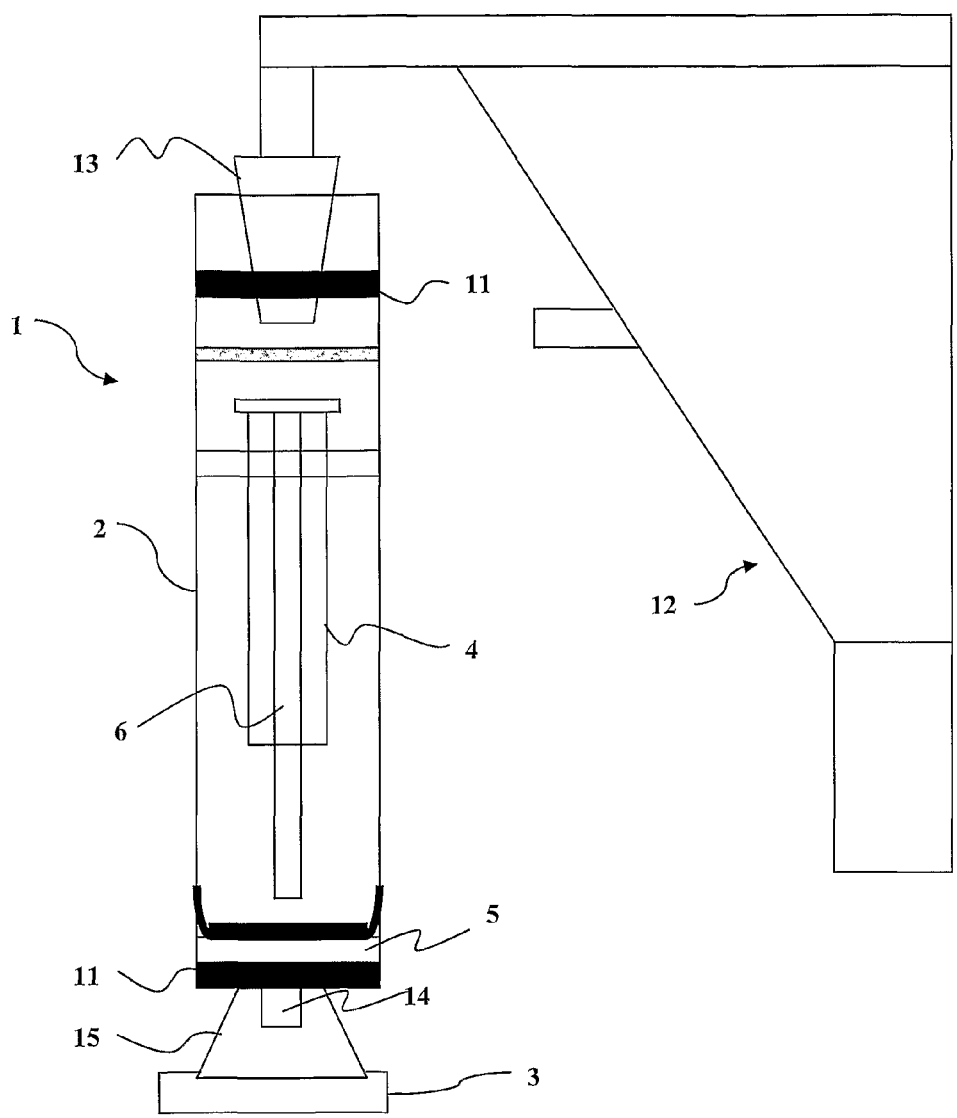
Figure 4:
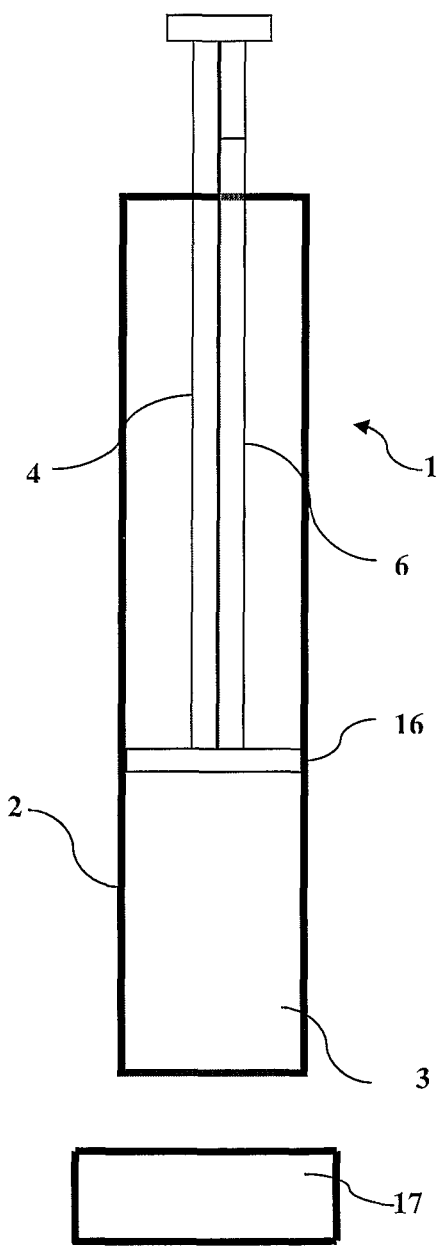
Figure 5:
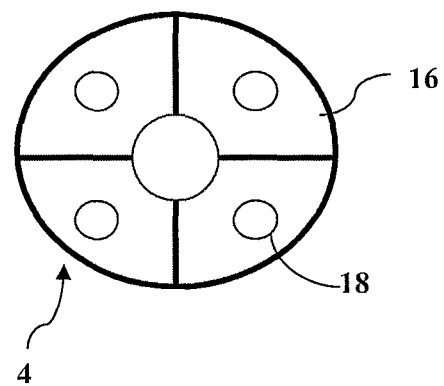

The present invention will now be described with reference to the following non-limiting examples and drawings in which FIG. 1 shows an embodiment of the device of the first aspect comprising a female member and a corresponding male member which is capable of detecting a target analyte, FIGS. 2 $a$), $b$), $c$) and $d$) illustrates the process of detecting a target analyte with the device of FIG. 1, FIG. 3 shows an embodiment of the device of the second aspect wherein suction may be applied to enable detection of a target analyte, FIG. 4 shows an embodiment of the device of the first aspect wherein the absorbent material may be compressed by the male member to facilitate detection of a target analyte. The device is based on the design of a syringe wherein the male member is the plunger of the syringe, FIG. 5 shows an exploded plan view of the male member/plunger from the device of FIG. 4.

EXAMPLES

Example 1

Referring now to FIG. 1, device 1 comprises a vessel (female member) 2 containing an absorbent material 3, a filtration material 5, and a male member 4 for supporting one or more detection means, such as lateral flow test strips 6. The absorbent material 3 is situated at one end, i.e. the bottom, of vessel 2, and is available such to contact a surface through an opening within the underside of 2. A fluid may be preabsorbed to the absorbent material. Filtration material 5 is in contact with the upper surface of absorbent material 3. Male member 4 is situated within vessel 2 such that it is not in contact with filtration material 5, however male member 4 is movably disposed within vessel 2, such that it may contact filtration material 5 in response to a force, such as may be exerted by a finger or hand of the user of the device. Male member 4 is therefore available to the user of the device through an opening in the top of vessel 2. The lateral flow test strips 6 are supported by male member 4 such that test strips 6 may also contact filtration material 5 in response to a force exerted on male member 4.

Referring now to FIGS. 2 *a*), *b*), *c*) and *d*), device 1 of FIG. 1 may be contacted with a surface 7 containing a target analyte 8 and particulates 9 (FIG. 2*a*). Upon contact with the surface, the absorbent material 3, which has a fluid (buffer) absorbed to it, collects or absorbs both target analyte 8 and particulates 9 (FIG. 2*b*). By applying a downward force to male member 4 the lateral flow test strips 6 may communicate with absorbent material 3, through filtration material 5. Alternatively by applying a downward force to male member 4 pressure is applied to absorbent material 3, through filtration material 5, to release the absorbed fluid from absorbent material 3. Male member 4 may have an opening or orifice situated in its underside, i.e. the surface of male member 4 that contacts filtration material 5, which is larger in surface area than the opening in vessel 2 so that upon applying pressure to absorbent material 3 the fluid is retained in vessel 2, rather than being dispelled from vessel 2. The released fluid may then contact lateral flow test strips 6. Filtration material 5 allows passage of target analyte 8, dissolved or suspended in the fluid (buffer), such that it is available to contact test strips 6, but prevents passage of particulates 9 (FIG. 2*c*). Target analyte 8, in fluid (buffer), then proceeds along test strips 6 through capillary action, upon which a coloured band 10 on the test strip, denoting a positive or negative result, may occur (FIG. 2*d*).

Example 2

Referring now to FIG. 3, device 1 comprises a vessel 2 containing an absorbent material 3, a filtration material 5, and means 4 for supporting detection means, such as lateral flow test strips 6. The absorbent material 3 is situated at one end, i.e. the bottom, of vessel 2, and is available such to contact a surface. The vessel 2 comprises an opening for connecting the teat 13 of a 'pipette boy' 12 to device 1, such that in use the 'pipette boy' 12 can provide suction to device 1. Vessel 2 also has a small orifice 14 between filtration material 5 and absorbent material 3, and contains one or more seals 11 such that suction can be efficiently provided. Tapering 15 of vessel 2 from absorbent material 3 towards small orifice 14 may further enhance collection of liquid from a surface. In use, absorbent material 3 having a fluid absorbed to it may take up a target analyte from a dry surface, and then by providing suction with a 'pipette boy' 12 the fluid will be sucked through small orifice 14, through filtration material 5 and communicate with the lateral flow test strip 6.

Example 3

Referring now to FIG. 4 and FIG. 5, device 1 comprises a female member 2 containing an absorbent material 3, and a male member 4 supporting at least one lateral flow test strip. The absorbent material 3 is situated at one end, i.e. the bottom or base, of female member 2, and is available such to contact a surface through an opening within the underside of 2. A fluid may be preabsorbed to the absorbent material. The device is based on the design of a syringe wherein the male member is a plunger. The male member is thus capable of movement within the female member such that it may contact the absorbent material, and apply compression to the absorbent material. The head 16 of the plunger comprises orifices 18, and the device 1 comprises a cap 17 capable of sealing the opening in the base of female member 2. Thus, by attaching cap 17 to the device, and applying pressure to the absorbent material with male member 4, any fluid absorbed to the absorbent material will be forced through orifices 18 in plunger head 16 to contact with the lateral flow test strips 6.

Example 4

Recovery of Firefly Luciferase from a Surface

The efficiency and recovery of a soluble protein (firefly luciferase) from a surface with the device of FIG. 3 was evaluated. Phosphate buffered saline buffer (1 µl) containing 5 ng or $8.1 \times 10^6$ RLUs of firefly luciferase was pipetted onto a surface. The absorbent material (collector sponge) 3 was prewetted with a buffer containing 10 mM HEPES pH 7.5 and 0.005% (v/v) Tween 80. The absorbent material was contacted and moved over the surface whilst suction was applied via the "pipette boy" to collect the protein. The volume of liquid sucked into the device was between 2 and 3 ml. An aliquot of this liquid was then assayed for luciferase activity. The experiment was repeated six times. Recovery of firefly luciferase from the surface was between 16 and 38% recovery calculated using a luminescence based assay.

TABLE 1

Recovery of firefly luciferase from a surface with the device of FIG. 3.

| Experiment | Volume of buffer recovered (ml) | Total RLUs recovered | Enzyme activity recovered (%) |
| --- | --- | --- | --- |
| 1 | 3.0 | $1.5 \times 10^6$ | 18 |
| 2 | 2.5 | $3.1 \times 10^6$ | 38 |
| 3 | 2.5 | $1.0 \times 10^6$ | 12 |
| 4 | 3.0 | $2.7 \times 10^6$ | 33 |
| 5 | 2.5 | $2.0 \times 10^6$ | 25 |
| 6 | 2.5 | $1.3 \times 10^6$ | 16 |

Example 5

Recovery of Particulates from a Surface with the Device of FIG. 3

The ability of the device of FIG. 3 to collect particulates from the surface was assessed using latex beads. Deep blue dyed latex bead solution (10 µl) with beads of average diameter 0.8 µm (Sigma L1398) was pipetted onto a surface. The absorbent material (collector sponge) 3 was prewetted with buffer containing 10 mM HEPES pH 7.5 and 0.005% (v/v) Tween 80. The absorbent material was contacted and moved over the surface whilst suction was applied via the "pipette boy" to collect the particulates. The collected buffer was centrifuged. By visual examination it was estimated that approximately 50% of the latex particles were recovered from the surface.

Example 6

Detection of Ovalbumen from a Plastic Surface with the Device of FIG. 3

Ovalbumen (1 µl) at a concentration of 1 mg/ml or 0.1 mg/ml was pipetted onto a plastic surface, thus depositing 1 µg or 100 ng of protein, respectively. The absorbent material (collector sponge) 3 was prewetted with buffer containing 10 mM HEPES pH 7.5 and 0.005% (v/v) Tween 80. The absorbent material was contacted and moved over the surface whilst suction was applied to collect the protein. Fluid absorbed to the absorbent layer was communicated with an antibody test strip supported within the device. The antibody test strip was specific for ovalbumen, and produced a detectable positive result (by eye) for both concentrations of ovalbumen investigated.

Example 7

Detection of *Bacillus globigii* Spores from a Plastic Surface with the Device of FIG. 3

*Bacillus globigii* spore suspension (1 μl; $5 \times 10^6$ cfu total) was pipetted onto the plastic surface. The absorbent material (collector sponge) 3 was prewetted with buffer containing 10 mM HEPES pH 7.5 and 0.005% (v/v) Tween 80. The absorbent material was contacted and moved over the plastic surface whilst suction was applied to collect the spores. Fluid absorbed to the absorbent layer was communicated with an antibody test strip supported within the device. The antibody test strip was specific for *Bacillus globigii*, and produced a detectable positive result (by eye).

Example 8

Comparison of the Compression Device of FIGS. 4 and 5 with a Conventional Lateral Flow Test Kit Using Cotton Swab Sampling and Collection A series of experiments were conducted on wood laminate and metal surfaces contaminated with ovalbumen (50, 100 and 1000 ng) or a suspension of *B. atrophaeus* spores (commonly called BG; $1 \times 10^4$, $1 \times 10^5$ and $1 \times 10^6$ spores) as target analyte dried onto the surfaces prior to analysis. The surface sampling area for the compression device was 49 cm², and for the cotton bud was 1.76 cm². Duplicate samples for each quantity of target analyte were collected by both methods from both surfaces and assayed either conventionally or through use of the compression device. A further experiment utilised the compression device comprising two lateral flow test strips, one specific to ovalbumen and the other to BG, to sample a wood laminate surface comprising 1 μg ovalbumen and $1 \times 10^6$ BG spores. Samples were collected into a buffer of 10 mM HEPES (pH 7.5) containing 0.005% (v/v) Tween 80. Lateral flow test strips were evaluated by eye, recorded using a digital camera, and assigned a positive (+) rating based on the intensity of the developed red line.

TABLE 2

Recovery of ovalbumen and BG spores from laminate wood and metal surfaces using the compression device of FIGS. 4 and 5.

| | Response on Test Strip | |
| --- | --- | --- |
| | metal surface | wood laminate surface |
| ovalbumen | | |
| 50 ng | ++++ | ++++ |
| 100 ng | ++++ | ++++ |
| 1 ug | ++++ | ++++ |
| BG spores | | |
| $1 \times 10^6$ | ++ | ++ |
| $1 \times 10^5$ | + | + |
| $1 \times 10^4$ | − | − |

TABLE 2-continued

Recovery of ovalbumen and BG spores from laminate wood and metal surfaces using the compression device of FIGS. 4 and 5.

| | Response on Test Strip | |
| --- | --- | --- |
| | metal surface | wood laminate surface |
| BG spores + ovalbumen | | |
| $1 \times 10^6$ + 1 ug | | ++ (BG spores) +++ (ovalbumen) |

Intensity of developed line of test strip:
++++ high intensity;
++ medium intensity,
+ low intensity;
− not detected.

TABLE 3

Recovery of ovalbumen and BG spores from laminate wood and metal surfaces using a conventional lateral flow test kit with cotton swab sampling.

| | Response on test strip | |
| --- | --- | --- |
| | metal surface | wood laminate surface |
| ovalbumen | | |
| 50 ng | ++++ | ++++ |
| 100 ng | ++++ | ++++ |
| 1 ug | ++++ | ++++ |
| BG spores | | |
| $1 \times 10^6$ | ++ | ++ |
| $1 \times 10^5$ | + | + |
| $1 \times 10^4$ | − | − |

Intensity of developed line of test strip:
++++ high intensity;
++ medium intensity,
+ low intensity;
− not detected.

The compression device of FIGS. 4 and 5 is thus capable of sampling and detecting similar concentrations of target analyte as the conventional lateral flow test kit. It is however an improvement over the conventional test kit in that the compression device is designed to sample a much larger surface area, and indeed has been shown to sample and positively identify target analyte from a surface area approximately 30 times larger than that for a cotton swab with the same detection response.

The invention claimed is:

1. A device for detecting multiple target analytes on a surface comprising:
    (a) a female member having a first region situated at an upper opening end of the female member and a second base region situated at a base of the female member, the second base region comprising (i) an orifice and (ii) an absorbent material supported within the second base region which is externally available through the orifice and that can absorb the target analyte,
    (b) a plunger engaged within the first region of the female member which is capable of movement within the female member in response to an applied force, the plunger comprising (i) multiple detection means to detect the multiple target analytes and (ii) a head comprising multiple orifices; and
    (c) a removable cap for sealing the orifice in the second base region of the female member, wherein in use, the orifice in the second base region contacts a surface to absorb fluid containing the multiple target analytes, the removable cap is attached to seal the orifice in the second base region to prevent the fluid from being dispelled from the device, and external force is applied to the plunger which applies pressure to the absorbent material to cause fluid containing the multiple target analytes absorbed to the absorbent material to be forced through the multiple orifices in the plunger head and to contact the multiple detection means.

2. A device according to claim 1, in which the multiple detection means comprise multiple lateral flow test strips.

3. A device according to claim 1, further comprising a filter material or filter layer situated between the absorbent material and the multiple detection means.

4. A device according to claim 3, in which the filter material or filter layer is in contact with the absorbent material, and is discrete from the multiple detection means.

5. A device according to claim 1, in which the device is transparent or comprises a window to enable visual inspection of any visual indication of a positive and/or negative result produced by the multiple detection means.

6. A device according to claim 1, in which the absorbent material is prewetted with a buffer fluid.

7. A device according to claim 6 further comprising means for preventing loss or evaporation of the buffer fluid from the absorbent material.

8. A device according to claim 7, in which the means for preventing loss of evaporation comprises one or more airtight foil seals.

9. A method for detecting a target analyte on a surface comprising:
   (a) providing a device of claim 1;
   (b) absorbing a buffer fluid to the absorbent material of the device;
   (c) contacting the absorbent material with the surface;
   (d) applying pressure to the absorbent material by the plunger to enable release of the majority of the fluid into the device and facilitates communication of the fluid to the multiple detection means; and
   (e) detecting the target analyte through a measurable response provided by the multiple detection means.

\* \* \* \* \*